US007037707B2

(12) United States Patent
Webster et al.

(10) Patent No.: US 7,037,707 B2
(45) Date of Patent: May 2, 2006

(54) METHOD FOR GENERATING INFLUENZA VIRUSES AND VACCINES

(75) Inventors: Robert Gordon Webster, Memphis, TN (US); Richard John Webby, Memphis, TN (US); Hiroichi Ozaki, Memphis, TN (US)

(73) Assignee: St. Jude Children's Research Hospital, Memphis, TN (US)

( * ) Notice: Subject to any disclaimer, the term of this patent is extended or adjusted under 35 U.S.C. 154(b) by 226 days.

(21) Appl. No.: 10/654,737

(22) Filed: Sep. 4, 2003

(65) Prior Publication Data

US 2005/0054846 A1 Mar. 10, 2005

(51) Int. Cl.
C12N 7/00 (2006.01)
C12Q 1/70 (2006.01)
A01N 63/00 (2006.01)
(52) U.S. Cl. .................... 435/235.1; 435/5; 435/320.1; 424/93.6; 424/206.1; 930/220
(58) Field of Classification Search ............. 424/206.1, 424/199.1, 209.1; 435/235.1, 236, 320.1
See application file for complete search history.

(56) References Cited

U.S. PATENT DOCUMENTS

| | | | | |
|---|---|---|---|---|
| 5,824,536 A | * | 10/1998 | Webster et al. | 435/235.1 |
| 6,344,354 B1 | * | 2/2002 | Webster et al. | 435/235.1 |
| 6,468,544 B1 | * | 10/2002 | Egorov et al. | 424/209.1 |
| 6,544,785 B1 | * | 4/2003 | Palese et al. | 435/325 |
| 6,573,079 B1 | * | 6/2003 | Palese et al. | 435/235.1 |
| 6,635,416 B1 | * | 10/2003 | Palese et al. | 435/5 |
| 6,669,943 B1 | * | 12/2003 | Palese et al. | 424/199.1 |
| 6,800,288 B1 | * | 10/2004 | Ferko et al. | 424/199.1 |
| 2002/0164770 A1 | | 11/2002 | Hoffmann | |
| 2003/0035814 A1 | | 2/2003 | Kawaoka | |

OTHER PUBLICATIONS

Egorov, A. et al. Transfectant Influenza A Viruses with Long Deletions in the NS1 Protein Grow Efficiently in Vero Cells (Aug. 1998) Journal of Virology, 72(8):6437-6441.*
Talon, J. et al. Influenza A and B vaccines expressing altered NS1 proteinsL A vaccine approach (Apr. 2000) Proc. Natl. Acad. Sci. 97(8):4309-4314.*
Schickli, J.H. et al. Plasmid-only Rescue of influenza A virus vaccine candidates (2001) Phil. Trans. R. Soc. Lond. 356 (1416):1965-73.*
Enami, M. et al. Characterization of influenza Virus NS1 Protein by Using a Novel Helper-Virus-Free Reverse Genetic System (2000) Journal of Virology, 74(12):5556-5561.*
Salvatore, M. et al. Effects of Influenza A Virus NS1 Protein on Protein Expression: the NS1 Protein Enhances Translation and Is Not Required for Shutoff of Host Protein Synthesis (Feb. 2002) J. Virol. 76(3):1206-1212.*
Garcia-Sastre, A. et al. Influenza A Virus Lacking the NS1 Gene Replicates in Interferon-Deficient Systems (1998) Virology, 252:324-330.*
Lau, S.C.; Scholtissek, C,. "Abortive Infection of Vero Cells by an Influenza A Virus (FPV)" *Virology*, 212:225-231 (1995).
Palase, P., et al. "Negative-strand RNS viruses: Genetic engineering and applications" *PNAS*, 93:11354-11358 (1996).
Fodor, E.; et al. "Rescue of Influenza A Virus from Recombinant DNA" *Journal of Virology*, 73:9679-9682.
Subbarao, K.; et al., "Evaluation of a Genetically Modified Reassortant H5N1 Influenza A Virus Vaccine Candidate Generated by Plasmid-Based Reverse Genetics" *Virology*, 305:192-200 (2003).
Stohr, K. "The Global Agenda on Influenza Surveillance and Control" *Vaccine*, 21:1744-1748 (2003).
Govorkova, E.A.., et al. "Growth and Immunogenicity of Influenza Virusesz Cultivated in Vero or MDCK Cells And Embryonated Chicken Eggs" *Dev Biol Stand* 98:39-51 (1999).

(Continued)

*Primary Examiner*—Shanon Foley
*Assistant Examiner*—M. Franco Salvoza
(74) *Attorney, Agent, or Firm*—Shawn A. Hawkins

(57) ABSTRACT

The present invention is based on the discovery that a high titer reassortant influenza virus is produced in mammalian cell culture by replacing the NS gene of the A/PuertoRico/3/24 master strain with the NS gene of the A/England/1/53 strain. The invention provides influenza viruses and vaccines generated in mammalian cells as well as methods for producing such. The invention further provides an influenza virus master strain and kits for generating reassortant influenza viruses in mammalian cell culture and methods of making and using the master strain.

16 Claims, 2 Drawing Sheets

OTHER PUBLICATIONS

Govorkova, E.A., et al. "Replication of Influenza A viruses in a Green Monkey Kidney Continous Cell Line (Vero)" *Journal of Infectious Diseases* 172:250-253 (1995).

Govorkova, E.A. et al. "African Green Monkey Kidney (Vero) Cells Provide an Alternative Host Cell System for Influenza A and B Viruses" *Journal of Virology* 70:5519-5524 (1996).

Hoffman, E., et al. "A DNA Transfection System for Generations of Influenza A Virus from Eight Plasmids" *PNAS* 97:6108-6113 (2000).

Neumann, G., et al. "Generation of Influenza A Viruses entirely from Cloned cDNAs" *PNAS* 96:9345-9350 (1999).

Palese, P., et al "Influenza vaccines: present and future" *J. Clin. Invest* 110:9-13 (2002).

Neumann, G. et al. "Genetic Engineering of Influenza and Other Negative-Strand RNA Viruses Containing Segmented Genomes", *Advances in Virus Research* 53:265-300 (1999).

\* cited by examiner

NS1 alignment

```
M D P N T V S S F Q    V D C F L W H V R K    A/England/1/53 (SEQ ID NO:3)
. . . . . . . . . .    . . . . . . . . . .    A/England/1/53/v-a (SEQ ID NO:5)

Q V A D Q E L G D A    P F L D R L R R D Q    A/England/1/53 (SEQ ID NO:3)
R . . . . . . . . .    . . . . . . . . . .    A/England/1/53/v-a (SEQ ID NO:5)

K S L R G R G S T L    G L N I E T A T R V    A/England/1/53 (SEQ ID NO:3)
. . . . . . . . . .    . . . . . . I . A      A/England/1/53/v-a (SEQ ID NO:5)

G K Q I V E R I L K    E E S D E A L K M T    A/England/1/53 (SEQ ID NO:3)
. . . . . . . . . .    . . . . . . . . . .    A/England/1/53/v-a (SEQ ID NO:5)

M A S A P A S R Y L    T D M T I E E M S R    A/England/1/53 (SEQ ID NO:3)
. . . . . . . . . .    . . . . . . . . . .    A/England/1/53/v-a (SEQ ID NO:5)

D W F M L M P K Q K    V A G P L C I R M D    A/England/1/53 (SEQ ID NO:3)
. . . . . . . . . .    . . . . . . . . . .    A/England/1/53/v-a (SEQ ID NO:5)

Q A I M D K N I I L    K A N F S V I F D R    A/England/1/53 (SEQ ID NO:3)
. . . . . . S . . .    . . . . . . . . . .    A/England/1/53/v-a (SEQ ID NO:5)

L E T L I L L R A F    T E E G A I V G E I    A/England/1/53 (SEQ ID NO:3)
. . . . . . . . . .    . . . . . . . . . .    A/England/1/53/v-a (SEQ ID NO:5)

S P L P S L P G H T    N E D V K N A I G V    A/England/1/53 (SEQ ID NO:3)
. . . . . . . . . .    . . . I . . . . . .    A/England/1/53/v-a (SEQ ID NO:5)

L I G G L E W N D N    T V R V S K T L Q R    A/England/1/53 (SEQ ID NO:3)
. . . . . . . . N .    . . . . . . . . . .    A/England/1/53/v-a (SEQ ID NO:5)

F A W R S S N E N G    R P P L T P K Q K R    A/England/1/53 (SEQ ID NO:3)
. . . . . . . . . .    . . . . . . . . . .    A/England/1/53/v-a (SEQ ID NO:5)

K M A R T I R S E V    R R N K M A D Y        A/England/1/53 (SEQ ID NO:3)
. . . . . . . . . .                           A/England/1/53/v-a (SEQ ID NO:5)
```

Figure 1

NS2 alignment

```
M D P N T V S S F Q   D I L M R M S K M Q    A/England/1/53 (SEQ ID NO:4)
. . . . . . . . . .   . . . . I . . . . .    A/England/1/53/v-a (SEQ ID NO:6)

L G S S S E D L N G   M I T Q F E S L K L    A/England/1/53 (SEQ ID NO:4)
. . . . . . . . . .   I . . . . . . . . .    A/England/1/53/v-a (SEQ ID NO:6)

Y R D S L G E A V M   R M G D L H S L Q N    A/England/1/53 (SEQ ID NO:4)
. . . . . . . . . .   . . . . . . . . . .    A/England/1/53/v-a (SEQ ID NO:6)

R N G K W R E Q L G   Q K F E E I R W L I    A/England/1/53 (SEQ ID NO:4)
. . . . . . . . . .   . . . . . . . . . .    A/England/1/53/v-a (SEQ ID NO:6)

E E V R H K L K I T   E N S F E Q I T F M    A/England/1/53 (SEQ ID NO:4)
. . . . . R . . . .   . . . . . . . . . .    A/England/1/53/v-a (SEQ ID NO:6)

Q A L Q L L F E V E   Q E I R T F S F Q L    A/England/1/53 (SEQ ID NO:4)
. . . . . . L . . .   . . . . . . . . . .    A/England/1/53/v-a (SEQ ID NO:6)

I .                                          A/England/1/53 (SEQ ID NO:4)
. .                                          A/England/1/53/v-a (SEQ ID NO:6)
```

Figure 2

SEQUENCE LISTING

```
<160> NUMBER OF SEQ ID NOS: 6

<210> SEQ ID NO 1
<211> LENGTH: 824
<212> TYPE: DNA
<213> ORGANISM: Influenza A virus

<400> SEQUENCE: 1
acataatgga tcccaacact gtgtcaagct ttcaggtaga ttgcttcctt tggcatgtcc     60
gcaaacaagt tgcagaccaa gaactaggtg atgccccatt ccttgatcgg cttcgccgag    120
atcagaagtc cctaagggga agaggcagca ctctcggtct gaacatcgaa acagccaccc    180
gtgttggaaa gcagatagtg gagaggattc tgaaggaaga atccgatgag gcacttaaaa    240
tgaccatggc ctccgcacct gcttcgcgat acctaactga catgactatt gaggaaatgt    300
caagggactg gttcatgcta atgcccaagc agaaagtggc aggccctctt tgtatcagaa    360
tggaccaggc gatcatggat aagaacatca tactgaaagc gaatttcagt gtgatttttg    420
accggctgga gaccctaata ttactaaggg ctttcaccga agagggagca attgttggcg    480
aaatttcacc attgccttct cttccaggac atactaatga ggatgtcaaa aatgcaattg    540
gggtcctcat cggaggactt gaatggaatg ataacacagt tcgagtctct aaaactctac    600
agagattcgc ttggagaagc agtaatgaga atgggagacc tccactcact ccaaaacaga    660
aacggaaaat ggcgagaaca attaggtcag aagttcgaag aaataagatg gctgattgaa    720
gaagtgagac acaaattgaa gataacagag aatagttttg agcaaataac atttatgcaa    780
gccttacagc tactgtttga agtggaacaa gagataagaa cttt                     824

<210> SEQ ID NO 2
<211> LENGTH: 824
<212> TYPE: DNA
<213> ORGANISM: Influenza A virus
```

-continued

<400> SEQUENCE: 2

```
acataatgga tcccaacact gtgtcaagct ttcaggtaga ttgctttctt tggcatgtcc      60
gcaaacgagt tgcagaccaa gaactaggtg atgccccatt ccttgatcgg cttcgccgag     120
atcagaagtc cctaagagga gaggcagca ctctcgggct gaacatcgaa acagccatcc      180
gtgctggaaa gcaaatagtg gagcggattc tgaaggaaga atccgatgag gcacttaaaa    240
tgaccatggc ctctgcacct gcttcgcgct acctaactga catgactatt gaggaaatgt    300
caagggactg gttcatgctc atgcccaagc agaaagtggc aggccctctt tgtatcagaa    360
tggaccaggc gatcatggat aagagcatca tactgaaagc gaacttcagt gtgattttg    420
accggctgga gactctaata ttactaaggg ctttcaccga gagggagca attgttggcg    480
aaatttcacc attgccttct cttccaggac atactaatga ggatatcaaa aatgcaattg    540
gggtcctcat cggaggactt gaatggaata ataacacagt tcgagtctct aaaactctac    600
agagattcgc ttggagaagc agtaatgaga atgggagacc tccactcact ccaaaacaga    660
aacggaaaat ggcgagaaca attaggtcag aagtttgaag aaataagatg gttgattgaa    720
gaagtgagac acagactgaa gataacgag aatagttttg agcaaataac gtttatgcaa    780
gccttacagc tattgcttga agtggagcaa gagataagaa cttt                      824
```

<210> SEQ ID NO 3
<211> LENGTH: 238
<212> TYPE: PRT
<213> ORGANISM: Influenza A virus

<400> SEQUENCE: 3

```
Met Asp Pro Asn Thr Val Ser Ser Phe Gln Val Asp Cys Phe Leu Trp
 1               5                  10                  15

His Val Arg Lys Gln Val Ala Asp Gln Glu Leu Gly Asp Ala Pro Phe
            20                  25                  30

Leu Asp Arg Leu Arg Arg Asp Gln Lys Ser Leu Arg Gly Arg Gly Ser
        35                  40                  45

Thr Leu Gly Leu Asn Ile Glu Thr Ala Thr Arg Val Gly Lys Gln Ile
    50                  55                  60

Val Glu Arg Ile Leu Lys Glu Glu Ser Asp Glu Ala Leu Lys Met Thr
65                  70                  75                  80

Met Ala Ser Ala Pro Ala Ser Arg Tyr Leu Thr Asp Met Thr Ile Glu
                85                  90                  95

Glu Met Ser Arg Asp Trp Phe Met Leu Met Pro Lys Gln Lys Val Ala
            100                 105                 110

Gly Pro Leu Cys Ile Arg Met Asp Gln Ala Ile Met Asp Lys Asn Ile
        115                 120                 125

Ile Leu Lys Ala Asn Phe Ser Val Ile Phe Asp Arg Leu Glu Thr Leu
    130                 135                 140

Ile Leu Leu Arg Ala Phe Thr Glu Glu Gly Ala Ile Val Gly Glu Ile
145                 150                 155                 160

Ser Pro Leu Pro Ser Leu Pro Gly His Thr Asn Glu Asp Val Lys Asn
                165                 170                 175

Ala Ile Gly Val Leu Ile Gly Gly Leu Glu Trp Asn Asp Asn Thr Val
            180                 185                 190

Arg Val Ser Lys Thr Leu Gln Arg Phe Ala Trp Arg Ser Ser Asn Glu
        195                 200                 205

Asn Gly Arg Pro Pro Leu Thr Pro Lys Gln Lys Arg Lys Met Ala Arg
```

```
                    210                 215                 220
Thr Ile Arg Ser Glu Val Arg Arg Asn Lys Met Ala Asp Tyr
225                 230                 235

<210> SEQ ID NO 4
<211> LENGTH: 121
<212> TYPE: PRT
<213> ORGANISM: Influenza A virus

<400> SEQUENCE: 4

Met Asp Pro Asn Thr Val Ser Ser Phe Gln Asp Ile Leu Met Arg Met
1               5                   10                  15

Ser Lys Met Gln Leu Gly Ser Ser Ser Glu Asp Leu Asn Gly Met Ile
            20                  25                  30

Thr Gln Phe Glu Ser Leu Lys Leu Tyr Arg Asp Ser Leu Gly Glu Ala
        35                  40                  45

Val Met Arg Met Gly Asp Leu His Ser Leu Gln Asn Arg Asn Gly Lys
50                  55                  60

Trp Arg Glu Gln Leu Gly Gln Lys Phe Glu Glu Ile Arg Trp Leu Ile
65                  70                  75                  80

Glu Glu Val Arg His Lys Leu Lys Ile Thr Glu Asn Ser Phe Glu Gln
                85                  90                  95

Ile Thr Phe Met Gln Ala Leu Gln Leu Leu Phe Glu Val Glu Gln Glu
            100                 105                 110

Ile Arg Thr Phe Ser Phe Gln Leu Ile
        115                 120

<210> SEQ ID NO 5
<211> LENGTH: 230
<212> TYPE: PRT
<213> ORGANISM: Influenza A virus

<400> SEQUENCE: 5

Met Asp Pro Asn Thr Val Ser Ser Phe Gln Val Asp Cys Phe Leu Trp
1               5                   10                  15

His Val Arg Lys Arg Val Ala Asp Gln Glu Leu Gly Asp Ala Pro Phe
            20                  25                  30

Leu Asp Arg Leu Arg Arg Asp Gln Lys Ser Leu Arg Gly Arg Gly Ser
        35                  40                  45

Thr Leu Gly Leu Asn Ile Glu Thr Ala Ile Arg Ala Gly Lys Gln Ile
        50                  55                  60

Val Glu Arg Ile Leu Lys Glu Glu Ser Asp Glu Ala Leu Lys Met Thr
65                  70                  75                  80

Met Ala Ser Ala Pro Ala Ser Arg Tyr Leu Thr Asp Met Thr Ile Glu
                85                  90                  95

Glu Met Ser Arg Asp Trp Phe Met Leu Met Pro Lys Gln Lys Val Ala
            100                 105                 110

Gly Pro Leu Cys Ile Arg Met Asp Gln Ala Ile Met Asp Lys Ser Ile
        115                 120                 125

Ile Leu Lys Ala Asn Phe Ser Val Ile Phe Asp Arg Leu Glu Thr Leu
        130                 135                 140

Ile Leu Leu Arg Ala Phe Thr Glu Glu Gly Ala Ile Val Gly Glu Ile
145                 150                 155                 160

Ser Pro Leu Pro Ser Leu Pro Gly His Thr Asn Glu Asp Ile Lys Asn
                165                 170                 175

Ala Ile Gly Val Leu Ile Gly Gly Leu Glu Trp Asn Asn Asn Thr Val
```

-continued

```
              180                 185                 190
Arg Val Ser Lys Thr Leu Gln Arg Phe Ala Trp Arg Ser Ser Asn Glu
            195                 200                 205

Asn Gly Arg Pro Pro Leu Thr Pro Lys Gln Lys Arg Lys Met Ala Arg
        210                 215                 220

Thr Ile Arg Ser Glu Val
225                 230

<210> SEQ ID NO 6
<211> LENGTH: 121
<212> TYPE: PRT
<213> ORGANISM: Influenza A virus

<400> SEQUENCE: 6

Met Asp Pro Asn Thr Val Ser Ser Phe Gln Asp Ile Leu Met Arg Ile
1               5                   10                  15

Ser Lys Met Gln Leu Gly Ser Ser Ser Glu Asp Leu Asn Gly Ile Ile
            20                  25                  30

Thr Gln Phe Glu Ser Leu Lys Leu Tyr Arg Asp Ser Leu Gly Glu Ala
        35                  40                  45

Val Met Arg Met Gly Asp Leu His Ser Leu Gln Asn Arg Asn Gly Lys
    50                  55                  60

Trp Arg Glu Gln Leu Gly Gln Lys Phe Glu Glu Ile Arg Trp Leu Ile
65                  70                  75                  80

Glu Glu Val Arg His Arg Leu Lys Ile Thr Glu Asn Ser Phe Glu Gln
                85                  90                  95

Ile Thr Phe Met Gln Ala Leu Gln Leu Leu Leu Glu Val Glu Gln Glu
            100                 105                 110

Ile Arg Thr Phe Ser Phe Gln Leu Ile
            115                 120
```

METHOD FOR GENERATING INFLUENZA VIRUSES AND VACCINES

GOVERNMENT INTEREST

This invention was made in part with U.S. Government support under National Institutes of Health grant NIAID N01 AI95357. The U.S. Government may have certain rights in this invention.

FIELD OF THE INVENTION

This invention relates to the generation of influenza viruses and vaccines. The invention also relates to methods for making and using high-titer reassortant viruses for generating vaccine compositions.

BACKGROUND

The influenza virus is responsible for a respiratory disease that may affect up to 20% of the population annually and, on average, kills approximately 20,000 people each year in the United States alone. Symptoms of the virus include sudden fever, chills, headache, myalgia, sore throat and a non-productive cough. Serious respiratory complications, including pneumonia, can develop. Recently, outbreaks of influenza A H5N1 have presented serious disease in humans and birds. Aquatic birds are the natural host for the influenza virus, making it impossible to eradicate the virus. Thus, the need for continued development of influenza treatments and vaccines.

The virus' success in causing disease is due to its ability to evade the immune system by undergoing antigenic change, which is believed to occur when a host is infected simultaneously with both an animal influenza virus and a human influenza virus. Influenza viruses have a segmented genome which contains eight negative-sense RNA (nsRNA) gene segments (PB2, PB1, PA, NP, M, NS, HA and NA) that encode at least 10 polypeptides, including RNA-directed RNA polymerase proteins (PB2, PB1 and PA), nucleoprotein (NP), neuraminidase (NA), hemagglutinin (subunits HA1 and HA2), the matrix proteins (M1 and M2) and the non-structural proteins (NS1 and NS2) (Krug et al., In The Influenza Viruses, R. M. Krug, ed., Plenum Press, N.Y., 1989, pp. 89–152). During reassortment in the host, the human virus may incorporate the animal HA or NA surface protein genes into its genome; thus, producing a new influenza subtype.

In addition to antigenic shift, viruses undergo antigenic drift, via point mutations in the HA and NA surface proteins. This also allows the virus to evade the immune system.

Current Methods for Preparing Vaccines

Until recently, the only influenza vaccines available in the United States were inactivated influenza vaccines. In June 2003, the FDA approved the use of a live attenuated influenza virus vaccine in healthy children and adolescents, 5–17 years of age, and healthy adults, 18–49 years of age. The current vaccines contain two components of influenza A, H1N1 and H3N2, and an influenza B component. Over the last several years, at least one of the components had to be changed each year due to antigenic drift. Clinical isolates of human influenza virus are taken from infected patients and are reasserted in embryonated chicken eggs with a laboratory-adapted master strain of high-growth donor virus, the A/PuertoRico/8/34 (PR8) influenza strain. The purpose of this reassortment is to increase the yield of candidate vaccine strains achieved by recombining at least the HA or NA genes from the primary clinical isolates, with the six internal genes of the master strain donor virus. This provides high growth reassortants having antigenic determinants similar to those of the clinical isolates (Wood, J. M. and Williams, M. S., Textbook of Influenza. Blackwell Science LTd, Oxford, 1998; Robertson et al, Biologicals, 20:213, 1992). Vaccines are prepared by growing this reassorted viral strain in embryonated eggs and then inactivating the purified virus by chemical means.

In the case of a pandemic, chicken eggs will likely be insufficient and suboptimal for influenza vaccine production. Disadvantages of using enbryonated chicken eggs are (1) the lack of reliable year-round supplies of high-quality eggs and the low susceptibility of summer eggs to influenza virus infection (Monto, A S et al., J. Clin Microbiol, 13:233–235, 1981, (2) cultivation of influenza A and B viruses in eggs can lead to the selection of variants characterized by antigenic and structural changes in the HA molecule (Katz, J M, et al., Virology 156:386–395, 1987; Robertson, J S., et al., Virology 143:166–174, 1985; Schild, G C., et al., Nature (London) 303:706–709, 1983), (3) the inability of some viruses to grow in embryonated eggs (Monto AS, et al., J. Clin. Microbiol. 13(1): 233–235, 1981) and (4) the presence of adventitious agents in eggs can jeopardize the preparation of live, attenuated influenza virus vaccines. The use of chicken eggs for inter-pandemic influenza vaccine production requires detailed planning up to six months prior to manufacture to ensure an adequate supply of embryonated eggs (Gerdil, C, Vaccine 21(16): 1776–1779, 2003).

New Methods—Reverse Genetics

Recently developed reverse-genetics systems, based entirely on cDNA, have allowed the manipulation of the influenza viral genome (Palese et., Proc. Natl. Acad. Sci. USA 93:11354, 1996; Neumann and Kawaoka, Adv. Virus Res. 53:265, 1999; Neumann et al., Proc. Natl. Acad. Sci. USA 96:9345, 1999; Fodor et al., J. Virol. 73: 9679, 1999). Furthermore, an eight plasmid system that expresses the nsRNAs from a pol I promoter and the coexpression of the polymerase complex proteins result in the formation of infectious influenza A virus (Hoffmann et al., Proc. Natl. Acad. Sci. USA 97:6108–6113, 2000). This technology allows the rapid production of "custom made" vaccines from cDNA for use in pandemic emergencies. It provides the capability to attenuate pathogenic strains (Subbarao, et al., Virology 305; 192–200, 2003) and eliminates the need to screen reassortant viruses for the 6+2 configuration. The major disadvantage associated with this methodology is the need to use vaccine approved cell lines.

Cell Lines

The commonly used cell lines for rescue of influenza viruses from cDNA are 293T and Madin-Darby canine kidney (MDCK) cells. The 293T cell line is a transformed cell line and is therefore unlikely to be used for human vaccine production, and there are concerns over the tumorogenic potential of MDCK cells (Govorkova E A, et al. J. Virol 70(8): 5519–5524, 2001). Additionally, the utilization of the host specific RNA polymerase I promoters in the reverse genetics systems limits the cell lines to those of human or primate origin.

African green monkey kidney (Vero) cells are characterized, approved and certified by the World Health Organization (WHO) for production of human vaccines. However, Vero cells, while certified, were previously found unsuitable for large-scale production of human influenza virus vaccines. For example, the growth of influenza B in Vero cells was greatly restricted as compared to MDCK cells (Nakamura et al., J. Gen. Virol. 56:199–202,1981). Additionally, attempts to use Vero cells to evaluate the rimantadine sensitivity of human H1N1 and H3N2 influenza A viruses gave ambiguous results, due to the low titers of viruses produced in these cells, as compared with MDCK cells (Valette et al., Antimicrobiol. Agent and Chemotherapy 37:2239–2240, 1993). Thus, these and other studies indicate that influenza viruses have not previously replicated well in Vero cells, making them unsuitable for large-scale vaccine production. (Demidova et al., Vopr. Virosol (Russian) 346–352, 1979); Lau & Scholtissek, Virology 212:225–231, 1995).

The most widely used master strain, A/PuertoRico/8/34, produces a high titer virus in MDCK cells after rescue in MDCK and 293T mixed culture, which is suitable for research purposes. However, it does not produce a high titer virus in Vero cells, mammalian cells approved for use in generating vaccine for humans. By passaging an H1N1 reassortant isolate, A/England/1/53, multiple times in Vero cells, Govorkova EA, et al., J. Infect. Dis. 172(1):250–253, 1995, derived a high-yielding influenza virus. This reassortant virus was reported to contain the surface glycoprotein genes from A/England/1/53 and the remaining genes from A/Puerto Rico/8/34 (H1N1), the commonly used vaccine master strain.

There is a great urgency to develop improved cell culture systems suitable for influenza vaccine production for use in humans, which is a priority for the World Health Organization (Stohr, Vaccine 21:1744–1748, 2003). Therefore, there is the need for a master strain of influenza that will produce high titer influenza virus in cells that have been approved for production of human vaccines.

SUMMARY OF THE INVENTION

The present invention discloses methods for producing influenza virus and vaccine compositions by transfecting into a host cell the PB2, PB1, PA, NP and M genes from the A/PuertoRico/8/34 influenza strain, the NS gene from the A/England/1/53 influenza strain and the HA and NA genes from an influenza virus of interest to produce a reassortant influenza virus capable of high titer growth in the host cell. The influenza NS gene encodes two different proteins, NS1 and NS2.

In an embodiment of the present invention, the NS gene has the sequence set forth in SEQ ID NO: 1 or SEQ ID NO: 2. In another embodiment of the present invention the NS1 and NS2 proteins have the sequence set forth in SEQ ID NO: 3 or 4. In a preferred embodiment the NS1 and NS2 proteins have the sequence set forth in SEQ ID NO: 5 or 6. In a preferred embodiment of the present invention NS1 of the original A/England/1/53 protein has amino acid changes at one or more of the following positions relative to SEQ ID NO: 5: 21, 58, 60, 127, 174 or 189 and the deletion of amino acids 231 through 238; and one or more amino changes to positions 16, 31, 86 or 107 of SEQ ID NO: 6 in the NS2 protein. In a most preferred embodiment the amino acid changes are Gln-21 to Arg, Thr-58 to Ile, Val-60 to Ala, Asn-127 to Ser, Val-174 to Ile, Asp-189 to Asn and the deletion of amino acids 231 through 238 in the NS1 protein (FIG. 1), and Met-16 to Ile, Met-31 to Ile, Lys-86 to Arg or Phe-107 to Leu in the NS2 protein (FIG. 2).

These methods utilize mammalian host cells, preferably, mammalian cells which have been approved for human vaccine production, more preferably, Vero cells.

As an influenza virus of interest, these methods may utilize human, avian, swine or equine influenza viruses. In a preferred embodiment of the present invention the influenza virus of interest is an influenza A virus other than A/England/ 1/53. The HA and NA genes from any virus may be transfected into cells with the master strain of the present invention to produce a virus strain that grows more efficiently in the host cell.

Furthermore, this invention discloses influenza virus and vaccine compositions produced by transfecting into a host cell the PB2, PB1, PA, NP and M genes from the A/PuertoRico/8/34 influenza strain, the NS gene from the A/England/1/53 influenza strain and the HA and NA genes from an influenza virus of interest to produce a reassortant influenza virus capable of high titer growth in the host cell.

The present invention also discloses a kit containing expression plasmids which contain the PB2, PB1, PA, NP and M genes from the A/PuertoRico/8/34 influenza strain and the NS gene from the A/England/1/53 influenza strain. The expression plasmids from such a kit may be transfected with expression plasmids containing the HA and NA genes from any virus of interest into cells in order to generate a virus capable of high titer growth in a cell line approved for vaccine manufacture.

The present invention also discloses methods for producing viruses and vaccines which incorporate a modified A/PuertoRico/8/34 master strain. In the modified A/PuertoRico/8/34 master strain, the NS gene of the original virus is replaced with the NS gene of the A/England/1/53 virus, thus producing a virus master strain capable of high titer growth in host cells. A host cell is infected with the virus master strain and an influenza virus strain of interest to allow the two strains to reassort, thus producing a different virus subtype that exhibits high growth in the host cell. Alternatively, expression plasmids containing the PB2, PB1, PA, NP and M genes from A/PuertoRico/8/34, the NS gene from A/England/1/53 and the HA and NA genes from an influenza virus of interest are transfected into a host cell to produce a high growth strain of virus.

DESCRIPTION OF THE FIGURES AND SEQUENCE LISTING

FIG. 1 shows the alignment of the original A/England/1/ 53 protein with an A/England 1/53 NS1 protein from a strain adapted to produce high virus yields in Vero cells (A/England/1/53/v-a). The dots in the Vero adapted NS1 sequence (bottom row) indicate that the amino acid at that position is the same amino acid found in the original A/England/1/53 strain (top row). The Vero adapted NS1 sequence differs from the original strain at positions 21, 58, 60, 127, 174, 189, and with the deletion of amino acids 231 through 238 from the Vero adapted protein.

FIG. 2 shows the alignment of the original A/England/1/ 53 protein with an A/England/1/53 NS2 protein from a strain adapted to produce high virus yields in Vero cells (A/England/1/53/v-a). The dots in the Vero adapted NS2 sequence (bottom row) indicate that the amino acid at that position is the same amino acid found in the original A/England/1/53 strain (top row). The Vero adapted NS2 sequence differs from the original strain at positions 16, 31, 86 and 107.

SEQ ID NO: 1 is a sequence listing of the NS gene from the original A/England/1/53 virus.

SEQ ID NO: 2 is a sequence listing of the NS gene from the A/England/1/53/v-a virus or the PR8/Eng-NS virus strain. It encodes the NS1 and NS2 proteins that contain the following changes: Gln-21 to Arg, Thr-58 to Ile, Val-60 to Ala, Asn-127 to Ser, Val-174 to Ile, Asp-189 to Asn and the deletion of amino acids 231–238 in the NS1 protein, and Met-16 to Ile, Met-31 to Ile, Lys-86 to Arg or Phe-107 to Leu in the NS2 protein.

SEQ ID NO. 3 is the amino acid sequence of the original A/England/1/53 NS2 protein.

SEQ ID NO: 4 is the amino acid sequence of the original A/England/1/53 NS2 protein.

SEQ ID NO: 5 is the amino acid sequence of the NS1 gene encoded by PR8/Eng-NS or the A/England/1/53/v-a gene. This protein differs from the NS1 protein of the original A/England/1/53 virus in that it contains an Arg-21, Ile-58, Ala-60, Ser-127, Ile-174, Asn-189, and it lacks amino acids 231 through 238.

SEQ ID NO: 6 is the amino acid sequence of the NS2 gene encoded by PR8/Eng-NS or the A/England/1/53/v-a gene. This protein differs from the NS2 protein of the original A/England/1/53 virus in that it contains an Ile-16, Ile-31, Arg-86, Leu-107.

DETAILED DESCRIPTION OF THE INVENTION

The present invention provides an influenza virus master strain that produces high titer virus in mammalian cells. Such master strain consists of expression plasmids that contain the PB2, PB1, PA, NP and M genes from the A/PuertoRico/8/34 virus strain and the NS gene from the A/England/1/53 virus strain. The HA and NA proteins from any virus of interest may be combined with such master strain to produce a high titer virus.

The present invention also provides reassortant influenza viruses and methods for generating such viruses by transfecting into a host cell expression plasmids that contain the PB2, PB1, PA, NP and M genes from the A/PuertoRico/8/34 virus strain, the NS gene from the A/England/1/53 virus strain, and the HA and NA genes from an influenza virus of interest.

Based on the observation of Govorkova EA, et al., J. Infect. Dis. 172(1):250–253, 1995, which described a master strain that produced high titer influenza virus in mammalian cells, applicants undertook studies to identify the molecular changes responsible for the A/England/1/53 vero-adapted (A/England/1/53/v-a) virus' high-yielding phenotype in Vero cells. The goal was to produce an altered A/PuertoRico/8/34 vaccine master strain adapted for optimal efficiency of viral rescue in the reverse genetics system for growth in Vero cells. Contrary to what was reported in the Govorkova et al. manuscript, sequence analysis of the complete genome of A/England/1/53/v-a showed that this high-yielding virus contained not only the HA and NA genes from A/England/1/53, but also the NS gene from this same strain. The remaining A/England/1/53/v-a proteins (PB2, PB1, PA, MP and M) had more than 99% nucleotide identity to those of A/PuertoRico/8/34. The NS gene from A/England/1/53/v-a had only 90% identity to the corresponding A/PuertoRico/8/34 gene, the HA gene had 98% identity and the NA gene 97% identity. Therefore, the greatest number of genetic changes between A/England/1/53/v-a and A/PuertoRico/8/34 was in the NS gene.

As used herein, a "reassortant" virus is a virus in which gene segments encoding antigenic proteins from a virus strain of interest (e.g. hemagluttinin and neuraminidase genes) are combined with gene segments encoding viral polymerase complex (PB2, PB1 and PA genes) or other similar genes (e.g., non-glycoprotein genes, including M genes and NS genes, and nucleoprotein (NP) genes) from viruses adapted for growth in culture (or attenuated viruses). The reassortant virus thus carries the desired antigenic characteristics in a background or master strain that permits efficient production in a host cell. Such a reassortant virus is a desirable "virus seed" for production of virions to produce vaccine (see Furminger, In: Nicholson, Webster and May (eds.), Textbook of Influenza, Chapter 24, pp. 324–332). The reassortant virus is preferably purified by a process that has been shown to give consistent results, before being inactivated or attenuated for vaccine production (see, e.g., World Health Organization TRS No. 673, 1982). In the present invention the master strain contains PB2, PB1, PA, NP and M genes from the A/PuertoRico/8/34 virus, NS from the A/England/1/53 virus, and the HA and NA genes from any virus strain.

As used herein, the NS gene originates from the A/England/1/53 virus, an influenza A virus strain obtained from the repository at St. Jude Children's Research Hospital, Memphis, Tenn., USA. The virus may contain one or more modifications that have been introduced in the noncoding region(s) and/or one or more modifications that have been introduced in the coding region(s). In a preferred embodiment, the NS gene of A/England/1/53 consists of the sequence of SEQ ID NO: 1. In a most preferred embodiment, the NS gene of A/England/1/53 consists of the sequence of SEQ ID NO:2. The NS1 protein encoded by SEQ ID NO: 1 has the amino acid sequence of SEQ ID NO: 3. The NS1 protein encoded by SEQ ID NO: 2 has the amino acid sequence of SEQ ID NO. 5.

As used here in PR8/Eng-NS represents the virus produced when expression plasmids containing 7 genes from A/PuertoRico/8/34 (PB2, PB1, PA, NP, M, HA and NA) were combined with the expression plasmid containing the NS gene from A/England/1/53/v-a in a virus rescue experiment. Virus rescue is described in Hoffmann et al., Proc. Natl. Acad. Sci. USA, 97:6108–6113, 2000. The NS gene sequence in A/England/1/53/v-a and PR8/Eng-NS are identical (SEQ ID NO:2).

Sequences for the A/PuertoRico/8/34 virus are found in GenBank Accession Nos. NC004518–NC004525.

A "virus of interest" is any influenza A virus. It can be a virus that produces disease in an animal or a strain of virus a person may wish to study in the laboratory. The strains of viruses include, but are not limited to, human, avian, swine and equine.

"Expression plasmid" is a DNA vector comprising an "inner transcription unit" and an "outer transcription unit". Expression plasmids may be used to generate any type of RNA virus, preferably positive or negative strand RNA viruses, segmented or unsegmented genome RNA viruses or double stranded RNA viruses. Expression plasmids of the present invention may be generated by, but are not limited to, methods disclosed in Neumann et al., Proc. Natl. Acad. Sci. USA 96:9345, 1999 and U.S. patent application Ser. No. 20030035814 or Hoffmann et al., Proc. Natl. Acad. Sci. USA 97:6108–6113, 2000 and U.S. patent application Ser. No. 20020164770.

The term "transfection" or "transfecting" means the introduction of a foreign nucleic acid into a cell so that the host cell will express the introduced gene or sequence to produce a desired polypeptide, coded by the introduced gene or sequence. The introduced gene or sequence may also be called a "cloned" or "foreign" gene or sequence, may include regulatory or control sequences, such as start, stop, promoter, signal, secretion, or other sequences used by a cell's genetic machinery. The gene or sequence may include nonfunctional sequences or sequences with no known function. A host cell that receives and expresses introduced DNA or RNA has been "transformed" and is a "transformant" or a "clone." The DNA or RNA introduced to a host cell can come from any source, including the same genus or species as the host cell, or from a different genus or species.

The present invention contemplates isolation or synthesis of genes encoding influenza viral proteins to be used in the invention, including a full length, or naturally occurring form of an influenza viral protein, and any antigenic fragments thereof from any influenza viral source. As used herein, the term "gene" refers to an assembly of nucleotides that encode a protein or proteins, and includes cDNA and viral genomic DNA nucleic acids.

An influenza gene of interest, whether viral genomic DNA or cDNA, can be isolated from any subtype of influenza virus. Methods for obtaining an influenza viral hemagglutinin gene, for example, are well known in the art (Sambrook, Fritsch & Maniatis, Molecular Cloning: A Laboratoiy Manual, Second Edition (1989) Cold Spring Harbor Laboratory Press, Cold Spring Harbor, N.Y.). Techniques for isolating viral RNA and transcribing it into cDNA are well known in the art (Hoffmann, et al., Proc. Natl. Acad. Sci. USA 97:6108–6113, 2000; Hoffmann, et al., Arch. Virology 146: 2275–2290, 2002).

Any influenza virus potentially can serve as the source for the HA and NA genes of interest. The DNA may be obtained by standard procedures known in the art from cloned DNA by chemical synthesis, by cDNA cloning, or by the cloning of genomic influenza viral DNA, or fragments thereof, purified from the desired cell (See, for example, Sambrook, Fritsch & Maniatis, Molecular Cloning: A Laboratoiy Manual, Second Edition (1989) Cold Spring Harbor Laboratory Press, Cold Spring Harbor, N.Y.; Glover, D. M., DNA Cloning: A Practical Approach, MRL Press, Ltd., Oxford, U.K. Vol. I, II, 1985).

Cell Lines

According to methods for reassorting viruses of the present invention, suitable host cells include embryonated egg cells, Vero cells or other mammalian cells, preferably ones approved and certified according to the WHO requirements for vaccine production (Mizrahi, ed., Viral Vaccines, Wiley-Liss, N.Y., pp. 39–60, 1990). Non-limiting examples of cell lines that can be suitable for methods, viruses and compositions used in the present invention, include, but are not limited to, mammalian fibroblast or cultured epithelial cells as continuous cell lines. Further non-limiting examples include Vero, MDCK, 293T, BK-21 and CV-1 cells, readily available from commercial sources (e.g., ATCC, Rockville, Md.).

WHO certified, or certifiable, continuous cell lines are preferred for producing influenza virus vaccines of the present invention. The requirements for certifying such cell lines include characterization with respect to at least one of genealogy, growth characteristics, immunological markers, virus susceptibility tumorigenicity and storage conditions, as well as by testing in animals, eggs, and cell culture. Such characterization is used to confirm that the continuous cell lines are free from detectable adventitious agents. In some countries, karyology may also be required. In addition, tumorigenicity is preferably tested in cells that are at the same passage level as those used for vaccine production.

It is preferred to establish a complete characterization of the continuous cell line to be used, so that appropriate tests for purity of the final product can be included. Data that can be used for the characterization of a continuous cell line to be used in the present invention includes (a) information on its origin, derivation, and passage history; (b) information on its growth and morphological characteristics; (c) results of tests of adventitious agents; (d) distinguishing features, such as biochemical, imunological, and cytogenetic patterns which allow the cells to be clearly recognized among other cell lines; and (e) results of tests for tumorigenicity. Preferably, the passage level, or population doubling, of the cell line used is as low as possible.

Vaccines

The present invention provides vaccines and methods for production of influenza vaccines for treating or preventing influenza viral infections. For the production of an influenza vaccine in Vero cells, five plasmids containing the non glycoprotein segments (e.g., PB2, PB1, PA, NP and M) from the high yield strain A/PuertoRico/8/34 and the NS gene from the A/England/1/53 influenza strain are co-transfected with two expression plasmids containing the HA and NA genes of an influenza virus of interest. Virus produced in accordance with the invention can be used in traditional or new approaches to vaccination (see Bilsel and Kawaoka, In: Nicholson, Webster and May (eds.), Textbook of Influenza, Chapter 32, pp. 422–434). In particular, the present invention overcomes defects of current technology, with respect to low influenza virus titers generated in Vero cells.

The present invention permits the rapid development of a high titer desired reassortment virus in Vero cells. Thus, it advantageously positions a vaccine manufacturer to generate a sufficient quantity of vaccine to meet public health needs and ensure standardization, which is an important requirement in the event of a pandemic when the rapid production of a vaccine is required. Because the vaccines of the invention permit production in an approved cell culture system, they avoid non-specific pathogens, bacteria, and allergenic proteins that may be present in vaccines prepared in embryonated eggs.

Adjuvants have been used with vaccines (e.g., influenza vaccines) (see Wood and Williams, In: Nicholson, Webster and May (eds.), Textbook of Influenza, Chapter 23, pp. 317–323). The term "adjuvant" refers to a compound or mixture that enhances the immune response to an antigen. An adjuvant can serve as a tissue depot that slowly releases the antigen and also as a lymphoid system activator that non-specifically enhances the immune response (Hood, et al., Immunology, Second Ed., Benjamin/Cummings: Menlo Park, Calif., p. 384, 1984). Often, a primary challenge with an antigen alone, in the absence of an adjuvant, is that the antigen will fail to elicit a humoral or cellular immune response. Adjuvants include, but are not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, and potentially useful human adjuvants such as BCG (bacille Calmette-Guerin) and Corynebacteriumparvum. An example of a preferred synthetic adjuvant is QS-21. Alternatively, or in addition, immunostimulatory proteins can be provided as an adjuvant or to increase the immune response to a vaccine. Preferably, the adjuvant is pharmaceutically acceptable.

The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

Inactivated Vaccines

Inactivated virus vaccines are well established for vaccinating against RNA viral infection (e.g., influenza) (see Nichol, In: Nicholson, Webster and May (eds.), Textbook of Influenza, Chapter 27, pp. 358–372). To prepare inactivated virus, the transfected virus is grown either in cell culture or in embryonated eggs. Virus can be inactivated by treatment with formaldehyde, beta-propiolactone, ether, ether with detergent (such as Tween-80), cetyl trimethyl ammonium bromide (CTAB) and Triton N101, sodium deoxycholate and tri(n-butyl) phosphate (Furminger, supra; Wood and Williams, supra). Inactivation can occur after or prior to clarification of allantoic fluid (from virus produced in eggs); the virions are isolated and purified by centrifugation (Furminger, supra, see p. 326). To assess the potency of the vaccine, the single radial immunodiffusion (SRD) test can be used (Schild et al, Bull. World Health Organ., 52:43–50 and 223–31, 1975; Mostow et al., J. Clin. Microbiol., 2:531, 1975). The inactivated vaccine can be administered intramuscularly by injection.

Attenuated Live Virus

Live, attenuated influenza virus vaccines, using reassortant virus of the invention, can also be used for preventing or treating influenza virus infection, according to known method steps: Attenuation is performed by any method well know in the art, preferably achieved through the use of reverse genetics.

Attenuating mutations can be introduced into influenza virus genes by site-directed mutagenesis to rescue infectious viruses bearing these mutant genes. Attenuating mutations can be introduced into non-coding regions of the genome, as-well as into coding regions. Such attenuating mutations can also be introduced into genes other than the HA or NA, e.g., the PB2 polymerase gene (Subbarao et al., J. Virol. 67:7223–7228, 1993). Thus, new viruses can also be generated bearing attenuating mutations introduced by site-directed mutagenesis, and such new viruses can be used in the production of live attenuated reassortants.

It is preferred that such attenuated viruses maintain the genes from the reassortant virus that encode antigenic determinants substantially similar to those of the original virus of interest. This is because the purpose of the attenuated vaccine is to provide substantially the same antigenicity as the original virus of interest, while at the same time lacking infectivity to the degree that the vaccine causes minimal chance of inducing a serious pathogenic condition in the vaccinated mammal.

Thus, the reassortant virus can be attenuated or inactivated, formulated and administered, according to known methods, as a vaccine to induce an immune response in a mammal. Methods are well-known in the art for determining whether such attenuated or inactivated vaccines have maintained similar antigenicity to that of the original virus of interest. Such known methods include the use of antisera or antibodies to eliminate viruses expressing antigenic determinants of the donor virus; chemical selection (e.g., amantadine or rimantidine); HA and NA activity and inhibition; and DNA screening (such as probe hybridization or PCR) to confirm that genes encoding the antigenic determinants (e.g., HA or NA genes) are not present in the attenuated viruses. See, e.g., Robertson et al., Giornale di Igiene e Medicina Preventiva 29.4–58, 1988; Kilbourne, Bull. M2 World Health Org. 41:643–645, 969; Aymard-Henry et al., Bull. World Health Org. 481:199–202, 1973; Mahy et al., J. Biol. Stand. 5:237–247, 1977; Barrett et al., Virology: A Practical Approach, Oxford IRL Press, Oxford, pp. 119–150, 1985; Robertson et al., Biologicals 20:213–220, 1992.

The vaccines of the present invention may be administered topically, parenterally, transmucosally, e.g. orally, nasally, or rectally, or transdermally. Administration that is parenteral, e.g., via intravenous injection, also includes, but is not limited to, intra-arteriole, intramuscular, intradermal, subcutaneous, intraperitoneal, intraventricular, and intracranial.

The subject of the present invention is also a kit containing reagents according to the invention for the generation of influenza viruses and vaccines. Contents of the kit include, but are not limited to, expression plasmids containing the A/PuertoRico/8/34 genes that encode the PB2, PB1, PA, NP and M genes and an A/England/1/53 NS gene. The kit may contain expression plasmids that contain the HA and NA genes from a particular virus. Expression plasmids containing no virus genes may also be included so that the individual user is capable of incorporating the HA and NA genes from any influenza virus of interest. Mammaliam cell lines may also be included with the kit, including but not limited to, Vero and MDCK. Other components such as buffers, controls, and the like, known to those of ordinary skill in art, may be included in such kits.

The present invention may be better understood by reference to the following non-limiting examples. These examples are presented to more fully illustrate the invention through the description of particular embodiments. These examples should in no way be construed as limiting the scope of the invention.

EXAMPLE 1

Materials and Methods

Viruses, Cells, and Plasmids

Influenza viruses were obtained from the repository at St. Jude Children's Research Hospital, Memphis, Tenn., USA and propagated in 10-day-old embryonated chickens' eggs. MDCK and WHO vaccine-approved Vero cells were obtained from the American Type Culture Collection, and maintained in minimal essential medium (MEM; Invitrogen) containing 10% fetal bovine serum (FBS).

The plasmids encoding the 8 gene segments of the high-growth PR8 virus (pHW191–pHW198) and the HA and NA of A/Panama/2007/99 (pHW444 and pHW446, respectively), A/New Caledonia/20/99 (pHW244 and pHW246, respectively), and A/quail/Hong Kong/G1/97 (pHW409 and pHW422, respectively) have been described (Hoffmann et al., Vaccine 20:3165, 2002). The plasmids encoding the 8 gene segments of A/teal/Hong Kong/W312/97 were the same as those used by Hoffmann et al., Proc. Natl. Acad. Sci. USA 97:6108–6113, 2000.

Viral RNA Extraction, Reverse-Transcriptase Polymerase Chain Reaction (rtPCR), and DNA Sequencing Total RNA was extracted from virus-infected allantoic fluid by using the RNeasy kit (Qiagen). Production of cDNA and PCR were carried out under standard conditions with previously described primers (Hoffmann, et al., Arch. Virology 146:2275–2289, 2001). The sequence of template DNA was determined by using synthetic oligonucleotides and rhodamine or dRhodamine dye-terminator cycle sequencing ready reaction kits with AmpliTaq DNA polymerase FS (Perkin-Elmer, Applied Biosystems Inc. [PE/ABI], Foster City, Calif.). Samples were subjected to electrophoresis, detection, and analysis on PE/ABI model 373, model 373 stretch, or model 377 DNA sequencers.

Viral Gene Cloning

Full-length cDNA copies of viral genes were amplified by rtPCR as described above. The PCR fragments were cloned into the vector pCRII-TOPO (Invitrogen) according to the manufacturer's instructions. After transformation of TOP10 cells (Invitrogen) and purification of the plasmid by using a plasmid midi kit (Qiagen), the plasmid was digested with the restriction enzyme BsmBI (New England Biolabs) and ligated into the vector pHW2000. All clones were confirmed by full-length sequencing.

Virus Rescue from Cloned cDNA

Vero cells were grown to 70% confluency in a 75 cm2 flask then trypsinized with trypsin-EDTA (Invitrogen) and resuspended in 10 ml of Opti-MEM I (Invitrogen). To 2 ml of cell suspension was added 20 ml of fresh Opti-MEM I, and 3 ml of this suspension was seeded into each well of a 6-well tissue culture plate (approximately 1×106 cells per well). The plates were incubated at 37° C. overnight. The following day, 1 µg of each plasmid and 16 µl of TransIT LT-1 (Panvera) transfection reagent were added to Opti-MEM I to a final volume of 200 µl and the mixture incubated at room temperature for 45 min. After incubation, the medium was removed from 1 well of the 6-well plate, 800 µl of Opti-MEM I added to the transfection mix, and this mixture added dropwise to the cells. Six hours later, the DNA-transfection mixture was replaced by Opti-MEM I. Twenty-four hours after transfection, 1 ml of Opti-MEM I containing L-(tosylamido-2-phenyl) ethyl chloromethyl ketone (TPCK)-treated trypsin (0.8 µg/ml) was added to the cells.

The efficiency of virus rescue was calculated by determining the number of plaque-forming units (pfu) in the culture supernatants at various intervals after transfection. The number of pfu's in MDCK cells was determined as previously described (Lau and Scholtissek, Virology 212: 225–231, 1995).

Viral Growth Kinetics in Vero Cells

The ability of viruses of different genotypes to grow in Vero cells was determined by analyzing multiple replication cycles. Before infection of Vero cells, the rescued viruses were amplified in 10-day-old embryonated chickens' eggs. Confluent Vero-cell monolayers grown on 25 cm2 plates were washed with phosphate-buffered saline, overlaid with 0.5 ml of diluted virus suspension (to achieve a multiplicity of infection [MOI] of 0.01 pfu/cell), and incubated at room temperature for 60 minutes. The virus suspension was then removed by aspiration and 3 ml of MEM containing 0.4 µg/ml of TPCK-trypsin was added. Twenty-four hours later, another 0.4 µg/ml TPCK-trypsin was added. Sample supernatants were collected at 12-hour intervals until 72 hours after inoculation. The virus titer of the sample was determined by plaque assay on MDCK cells or by hemagglutination assay with 0.5% chicken erythrocytes. Antigenic analysis was performed with polyclonal antisera against PR8 (H1N1), A/New Caledonia/20/99 (H1N1), A/Panama/2007/99 (H3N2), A/teal/Hong Kong/w312/97 (H6N1), and A/quail/Hong Kong/G1/97 in hemagglutination inhibition assay (Kida, et al., Virology 122:38–47, 1982).

Statistical Evaluation of Virus Replication

The viral growth curves were fitted with logistic function, a nonlinear regression model commonly used for modeling the sigmoid growth curves in biology and chemistry (Davidian and Gilitinan, Nonlinear Models for Repeated Measurement Data. Chapman & Hall, New York, 1996; O'Connel, et al., Chemometrics and Intelligent Laboratory Systems 20:97–114, 1993; Pinheiro and Bates, Mixed-Effects Model in S and S-PLUS, Springer, N.Y., 2000). The logistic function in this analysis is given by $Ln(Viral\ Titers)=\varnothing1/\{1+exp[(\varnothing2-t)/\varnothing3]\}$ where t is the time post inoculation (in hour); ø1 is the peak titers (in Ln(pfu/ml)); ø2 is the halftime to peak titers; and ø3 is the time from half to 73% peak titers. The model was fitted using a nonlinear least square procedure (1) implemented with statistical software S-PLUS (Pinheiro and Bates, Mixed-Effects Model in S and S-PLUS, Springer, N.Y., 2000). Each growth curve was fitted with data of three replicate experiments. Based on the estimates of parameters and their standard errors from fitted models, the parameters for different strains of viruses (PR8, PR8/Eng-NS, and W312) were compared using t-tests. Viral titers of A/PuertoRico/8/34 and PR8/Eng-NS were also compared with two-way analysis of variance (ANOVA) method separately at 12, 24, 36, and 48 hours post inoculation. The two factors of the two-way ANOVA are virus type and master strain backbone.

Results

The Effect of the NS Gene of A/England/53/v-a on the Efficiency of Virus Rescue from cDNA in Vero Cells The NS gene from A/England/1/53/v-a was cloned into the expression plasmid, pHW2000. One experiment contained the plasmids necessary to rescue A/PuertoRico/8/34, another to rescue a reassortant virus containing 7 genes of A/PuertoRico/8/34 and the NS gene of A/England/1/53/v-a ("PR8/Eng-NS"). The supernatants of each virus rescue experiment were assayed for viral titers at 12 hour intervals. The results showed that the rescue efficiency of the PR8/Eng-NS virus was superior to that of A/PuertoRico/8/34 at 12, 24 and 36 hours post transfection ($p<0.001$ by ANOVA analysis) demonstrating that the gene product(s) of the NS gene can influence viral growth characteristics in Vero cells. There was no significant difference between viral titers at times over 36 hours post transfection. The half time to peak titer was significantly ($P<0.0001$) reduced for PR8/Eng-NS when compared to that for A/PuertoRico/8/34 (17.8±0.6 hours and 22.9±0.7 hours, respectively).

To assess the suitability of the PR8/Eng-NS virus as a master strain for vaccine purposes, similar experiments were conducted in which the HA and NA of contemporary viruses were rescued. The HA and NA from H1N1 (A/New Caledonia/20/99), H3N2 (A/Panama/2007/990), H6N1 (A/teal/Hong Kong/W312/97) and H9N2 A/quail/Hong Kong/G1/97 viruses reassorted onto the A/PuertoRico/8/34 and PR8/Eng-NS backbones using reverse genetics in Vero cells. All the HA and NA combination were rescued on both backbones, although the kinetics of virus rescue was faster with the PR8/Eng-NS viruses.

Effects of the NS Gene from Eng53/v-a on Growth Characteristics of PR8 in Vero Cells To assess the effect of the replacement of the NS gene in A/PuertoRico/8/34 on subsequent virus amplification in Vero cells triplicate samples of near-confluent Vero cells were infected with A/PuertoRico/8/34 and PR8/Eng-NS at a low MOI (0.01) and virus replication followed by assaying culture supernatant every 12 hours. PR8/Eng-NS had a significantly (P<0.0001) lower half time to peak titer than did A/PuertoRico/8/34 (16.8±0.6 hours and 25.3±0.7 hours, respectively) although there was no significant difference in peak titers ($1.6 \times 10^7$ pfu/ml and $1.2 \times 10^7$ pfu/ml, respectively). Thus, the growth characteristics of A/PuertoRico/8/34 in Vero cells are improved by inclusion of the NS gene of A/England/1/53/v-a. Similar experiments were conducted with recombinant A/PuertoRico/8/34 and PR8/Eng-NS viruses carrying the surface glycoproteins of A/New Caledonia/20/99 (H1N1), A/Panama/2007/99 (H3N2), A/teal/Hong Kong/W312/97 (H6N1), and A/quail/Hong Kong/G1/97 (H9N2). The half times to peak virus yield were significantly (P<0.0001) lower in all PR8/Eng-NS viruses than in their A/PuertoRico/8/34 counterparts. Thus showing that the half time to peak yield of different subtypes of influenza virus in Vero cells is reduced by inclusion of the NS gene of A/England/1/53/v-a. The peak titers of the PR8/Eng-NS viruses carrying the surface glycoproteins of the A/New Caledonia/20/99 and A/Panama/2007/99 viruses were significantly higher (P<0.005) than those of the A/PuertoRico/8/34 viruses. The increase in growth kinetics in Vero cells did not affect the ability of the reassortant viruses to grow in eggs. The PR8/Eng-NS variants all grew to equivalent HA titers in eggs as their A/PuertoRico/8/34 counterparts.

In a related experiment the growth characteristics, in Vero cells, of 2 reverse-genetics derived viruses containing the HA and NA genes of A/teal/Hong Kong/W312/97 (W312) were compared with those of the reverse genetics derived wild-type W312. The remaining gene segments of the 2 variants were from A/PuertoRico/8/34 or PR8/Eng-NS. Although the peak titers of all 3 viruses at 72 hours were similar, the half times to peak titer were significantly (P<0.0001) shorter for the A/PuertoRico/8/34 and PR8/Eng-NS variants (29.3±1.0 and 20.7±0.8 hours, respectively) than for W312 (60.3±4.5 hours).

To test whether changes in genes other than NS could lead to further improvements in the growth characteristics of PR8/Eng-NS, we determined the growth characteristics of A/PuertoRico/8/34, Eng53/v-a, and PR8/Eng-NS in Vero cells. If further improvements were possible, they would be indicated by Eng53/v-a having superior growth characteristics to PR8/Eng-NS. The growth characteristics of Eng53/v-a and PR8/Eng-NS were substantially better than those of A/PuertoRico/8/34 but indistinguishable from each another. This result suggests that the high-yielding phenotype of Eng53/v-a is due solely to the NS gene.

Stability of Viruses Rescued from Vero Cells

Vaccine-production procedures must allow the virus produced to retain the antigenic properties of the parent viruses. Any benefit from an increase in yield would be negated by changes in the antigenicity of a vaccine. To determine whether antigenic changes occurred upon rescue of viruses in Vero cells we used hemagglutination inhibition assays to compare the antigenic profiles of the rescued PR8/Eng-NS viruses with their wild-type counterparts. All PR8/Eng-NS rescued viruses were antigenically indistinguishable from the corresponding wild-type viruses. To confirm the genetic stability of the PR8/Eng-NS rescued viruses, we compared the HA gene sequences of the rescued and wild-type viruses. We found no changes in any of the viruses. This result demonstrates that introduction of the NS gene from Eng53/v-a into the PR8 vaccine master strain does not lead to changes in the HA gene.

Discussion

Recent discoveries in influenza pathogenicity and reverse genetics have the potential to revolutionize the way pandemic and interpandemic influenza vaccines are prepared and manufactured. Much of this technology has, however, been confined to experimental protocols; the realization of this potential awaits refinements of the methods. By incorporating the NS gene of Eng53/v-a into the standard A/PuertoRico/8/34 vaccine master strain, we have shown a reproducible improvement in vaccine-virus rescue and growth in Vero cells with no drop in egg titers. Although these viruses were rescued with the standard A/PuertoRico/8/34 vaccine strain, the improved efficiency of rescue with the PR8/Eng-NS system may be crucial with other HA and NA combinations that are poorly infective in Vero cells.

With each of the HA and NA subtypes tested, the PR8/Eng-NS viruses reached peak titers significantly faster than did the corresponding A/PuertoRico/8/34 virus. The peak titers of the PR8/Eng-NS variants containing the surface glycoproteins of the 2 contemporary vaccine strains (A/New Caledonia/20/99 and A/Panama/2007/99) and of A/teal/Hong Kong/W312/97, a virus implicated in the genesis of the 1997 H5N1 human viruses (Hoffmann, E. J. et al., Virology 74:6309–6315, 2000), were also significantly higher than those of the PR8 viruses. In contrast, there was no difference in the peak titers of the PR8/Eng-NS and A/PuertoRico/8/34 viruses carrying the surface glycoproteins of A/quail/Hong Kong/G1/97 or A/PuertoRico/8/34 itself. However, by the time these peak titers were reached with the A/PuertoRico/8/34 variants, the cells infected with the PR8/Eng-NS variants had been completely destroyed by cytopathic effects and a manufacturing process in which cells and fresh media can be continually added or replenished is likely to produce higher yields for those viruses on the PR8/Eng-NS backbone.

This data also provides support for the continued use of 6+2 high-growth reassortants for vaccine production in Vero cells. For example, the PR8/Eng-NS variant of the H6N1 virus had significantly superior growth characteristics to those of the wild-type H6N1 virus; the estimates of half times to peak titers were 3 times longer in the wild-type virus. The use of 6+2 reassortants also reduces the risks of growing adventitious agents with influenza viruses isolated directly from clinical samples.

One of the benefits of cell-based production of vaccines is that it appears to allow the properties of influenza virus HA molecules to remain unchanged; these molecules are altered during the adaptation of viruses to eggs (Katz, J. M., et al., Virology 156:386–395, 1987; Robertson, J. S., Virology 143:166–174, 1985; Schild, J. H., et al, Nature 303:706–709, 1983). We found that the HA genes of the PR8/Eng-NS-derived viruses were the same before and after rescue and propagation from Vero cells. This stability is an advantage in a vaccine that derives much of its protective qualities from the production of neutralizing antibody directed against the HA molecule. However, such benefits will be lost unless candidate vaccine viruses are first isolated in approved cell lines rather than the widely used MDCK cells or eggs.

Host range in influenza viruses is a polygenic trait, for which many influenza proteins have been implicated (Hatta, M., et al, Virology 295:250–255, 2002; Scholtissek, C., et al., Virology 147:287–294, 1985; Snyder, M. H., et al., Virus Res. 15:69–83, 1990; Tian, S. F., et al., J. Virology 53:771–775, 1985). Likewise, many genes, including the NS gene, have been implicated in the attenuation of influenza viruses in different hosts (Clements, M. L., J. Clin. Microbiology 30:655–662, 1002; Maassab, H. F. and DeBorde, D. C., Virology 130:342–350, 1983; Snyder, M. H., et al., virus Res. 15:69–83, 1990). However, in our system, the transfer of the NS gene from Eng53/v-a to A/PuertoRico/8/34 was alone sufficient to confer the high-growth phenotype. Although many factors have been reported to determine the efficiency of growth of influenza viruses, the NS1 protein (1 of the 2 proteins expressed by the NS gene) is thought to play a significant role in translation and replication For example, NS1 and its interaction with host proteins have been reported to play central roles in inhibiting the nuclear export and splicing of host mRNA (Fortes, P., EMBO J. 13:704–712, 1994; Nemeroff, M. E., Mol. Cell 1:991–1000, 1998; Qiu, Y. and Krug, R. M., J. Virology 63:2425–2432, 1994, Qui, Y., et al., RNA 1:304–316, 1995; Wang, W. and Krug, R. M., RNA 4:55–64, 1998; Wolff, T., et al., J. Virology 72:7170–7180, 1998). Furthermore, NS1 protein plays an important role in regulating interferon activity (Seq, S. H., et al, Nat. Med. 8:950–954, 2002). It is unlikely, however, that the interferon pathway is involved in viral growth in Vero cells, because Vero cells do not produce interferon (Diaz, M. O., et al., Proc. Natl. Acad. Sci. USA 85;5259–5263, 1988). Another study failed to identify major changes in the shutoff of host protein synthesis or in viral protein expression in Vero cells after infection with NS1 deletion-mutant viruses (Salvatore, M., et al., J. Virology 76:1206–1212, 2002). Garcia-Sastre et al. showed, however, that a mutant virus that did not express NS 1 protein (de1NS1) grew approximately 10 times slower on Vero cells than did the wild-type strain (Garcia-Sastre, A., et al., Virology 252:324–330, 1998). The second protein encoded by the NS gene is the NS2 or nuclear export protein (NEP). Although little is known about the function of NEP, this polypeptide interacts with nucleoprotein and contributes to the nuclear export of the viral ribonucleoproteins (O'Neill, R. E., et al., EMBO J. 17:288–296, 1998). Additionally, amino acid residues of the NEP have been shown to be crucial for viral replication (Bullido, R., et al., J. Virology 75:4912–4917, 2001). Studies are ongoing to identify the NS gene products responsible for increased viral replication in Vero cells and the mechanisms involved.

The applicability of reverse genetics to the production of influenza vaccines depends on the use of a suitable cell culture system. Technical constraints and the limited number of cells licensed for vaccine production severely limit the options available. It is therefore likely that timely improvements in reverse genetics derived vaccines will arise from optimization of current protocols rather than identification of alternative systems. The use of the Vero-cell system with an improved master strain virus is a viable option for the rapid manufacture of influenza vaccines in pandemic emergencies and for the production of vaccines during annual epidemics.

---

We claim:

1. A method for producing a reassortant influenza virus comprising transfecting host cells with expression plasmids containing PB2, PB1, PA, NP and M genes from A/PuertoRico/8/34 influenza strain, an NS gene encoding an NS1 protein having an amino acid sequence comprising SEQ ID NO:5 and an NS2 protein having an amino acid sequence comprising SEQ ID NO:6, and HA and NA genes from an influenza virus of interest other than A/England/1/53, to obtain a reassortant influenza virus.

2. The method of claim 1 wherein the NS gene has a sequence set forth in SEQ ID NO: 2.

3. The method of claim 1 wherein said host cells are mammalian cells.

4. The method of claim 3 wherein said mammalian cells are selected from the group consisting of cells suitable for preparing vaccines for use in humans.

5. The method of claim 4 wherein said mammalian cells are Vero cells.

6. The method of claim 1 wherein said influenza virus of interest is selected from the group consisting of human, avian, swine and equine.

7. A reassortant influenza virus strain comprising a modified A/PuertoRico/8/34 influenza strain, wherein an NS gene of the A/PuertoRico/8/34 influenza strain is replaced with an NS gene encoding an NS1 protein having an amino acid sequence comprising SEQ ID NO:5 and an NS2 protein having an amino acid sequence comprising SEQ ID NO:6, and HA and NA genes from an influenza virus strain of interest other than A/England/1/53.

8. A method of producing a reassortant influenza virus vaccine comprising transfecting cells with expression plasmids containing the PB2, PB1, PA, NP and M genes from an A/PuertoRico/8/34 influenza strain, an NS gene encoding an NS1 protein having an amino acid sequence comprising SEQ ID NO:5 and an NS2 protein having an amino acid sequence comprising SEQ ID NO:6, and HA and NA genes from an influenza virus of interest other than A/England/1/53, to obtain a reassortant influenza virus vaccine.

9. A reassortant influenza virus vaccine comprising a modified A/PuertoRico/8/34 influenza strain and a pharmaceutically acceptable carrier, wherein an NS gene of the A/PuertoRico/8/34 influenza strain is replaced with an NS gene encoding an NS1 protein having an amino acid sequence comprising SEQ ID NO:5 and an NS2 protein having an amino acid sequence comprising SEQ ID NO:6, and HA and NA genes from an influenza virus strain of interest other than A/England/1/53.

10. The vaccine of claim 15, further comprising an adjuvant which enhances an influenza virus immune response.

11. A kit for producing an influenza virus master strain comprising expression plasmids containing PB2, PB1, PA, NP and M genes from an A/PuertoRico/8/34 influenza strain and an NS gene encoding an NS1 protein having an amino acid sequence comprising SEQ ID NO:5 and an NS2 protein having an amino acid sequence comprising SEQ ID NO:6.

12. A modified A/PuertoRico/8/34 influenza virus master strain, wherein PB2, PB1, PA, NP and M genes are from A/PuertoRico/8/34 influenza strain, a NS gene encoding an NS1 protein having an amino acid sequence comprising SEQ ID NO:5 and an NS2 protein having an amino acid sequence comprising SEQ ID NO:6, and HA and NA genes are from any influenza virus other than A/England/1/53.

13. A method of producing a reassortant influenza virus comprising infecting a host cell with the influenza virus master strain of claim 12 and an influenza virus of interest other than A/England/1/53, wherein the genes from the master strain and the virus of interest reassort in the host cell to produce a different virus strain.

14. An A/PuertoRico/8/34 master strain used for producing an influenza virus, the improvement which consists of replacing an NS gene of the A/PuertoRico/8/34 influenza strain with an NS gene encoding an NS1 protein having an amino acid sequence comprising SEO ID NO:5 and an NS2 protein having an amino acid sequence comprising SEO ID NO:6, and HA and NA genes from any influenza virus other than A/England/1/53.

15. A method for producing a reassortant influenza virus comprising transfecting host cells with expression plasmids containing PB2, PB1, PA, NP and M genes from A/PuertoRico/8/34 influenza strain, HA and NA genes from an influenza virus of interest other than A/England/1/53, and an NS gene encoding an NS1 protein having an amino acid sequence comprising SEQ ID NO:3 with one or more changes selected from the group consisting of amino acid substitutions at positions 21, 58, 60, 127, 174, and 189 and a deletion of amino acids 231–238 and encoding an NS2 protein having an amino acid sequence comprising SEQ ID NO:4 with one or more changes selected from the group consisting of amino acid substitutions at positions 16, 31, 86, and 107 to obtain a reassortant influenza virus.

16. The method of claim 15 wherein the substitution of the NS 1 amino acid sequence at position 21 is Gln to Arg, at position 58 is Thr to Ile, at position 60 is Val to Ala, at position 127 is Asn to Ser, at position 174 is Val to Ile, at position 189 is Asp to Asn, and the substitution of the NS2 amino acid sequence at position 16 is Met to Ile, at position 31 is Met to Ile, at position 86 is Lys to Arg, and at position 107 is Phe to Leu.

* * * * *

UNITED STATES PATENT AND TRADEMARK OFFICE
CERTIFICATE OF CORRECTION

PATENT NO. : 7,037,707 B2
APPLICATION NO. : 10/654737
DATED : May 2, 2006
INVENTOR(S) : Robert Gordon Webster, Richard John Webby and Hiroichi Ozaki It is certified that error appears in the above-identified patent and that said Letters Patent is hereby corrected as shown below:

At Column 22, line 61, please delete "The vaccine of claim 15" and insert therefore --The vaccine of claim 9--

Signed and Sealed this

Twenty-ninth Day of August, 2006

JON W. DUDAS
*Director of the United States Patent and Trademark Office*